United States Patent [19]

Franckowiak et al.

[11] 4,348,395
[45] Sep. 7, 1982

[54] 1,4-DIHYDROPYRIDAZINE COMPOUNDS

[75] Inventors: Gerhard Franckowiak; Horst Meyer; Friedrich Bossert; Arend Heise; Stanislav Kazda; Kurt Stoepel; Robertson Towart, all of Wuppertal; Egbert Wehinger, Velbert, all of Fed. Rep. of Germany

[73] Assignee: Bayer Aktiengesellschaft, Leverkusen, Fed. Rep. of Germany

[21] Appl. No.: 948,599

[22] Filed: Oct. 4, 1978

[30] Foreign Application Priority Data

Oct. 10, 1977 [DE] Fed. Rep. of Germany ....... 2745496

[51] Int. Cl.³ ..................... A61K 31/50; C07D 237/04
[52] U.S. Cl. .................................... 424/250; 424/251; 544/238; 544/224
[58] Field of Search ................. 544/238, 224; 424/250

[56] References Cited

U.S. PATENT DOCUMENTS 4,011,218 3/1977 Baldwin et al. ..................... 544/238
4,058,390 11/1977 Schönbeck et al. ................ 544/238

Primary Examiner—Anton H. Sutto
Assistant Examiner—James H. Turnipseed

[57] ABSTRACT

The invention includes, as novel compounds, 1,4-dihydropyridazines and methods for their preparation. Also included are compositions containing said compounds and methods for the use of said compounds and compositions. The compounds of the invention are active as circulation-influencing and spasmolytically active agents.

13 Claims, No Drawings

1,4-DIHYDROPYRIDAZINE COMPOUNDS

The present invention relates to certain new 1,4-dihydropyridazines, to a process for their production and to their use as pharmaceuticals in particular as circulation-influencing and spasmolytically active agents.

It has already been disclosed that N-substituted nitrogen-containing heterocyclic compounds are obtained when the anions of the heterocyclic compounds are reacted with electrophiles (compare N. Lubavin, Chem. Ber. 2, 100 (1869); A. Pictet, Chem. Ber. 37, 2,797 (1904); W. Tschelnisew and B. Marxorow, Chem. Ber. 60, 194, (1927), H. Staudinger and Sutter, Chem. Ber. 53, 1,104 (1920); and G. Giamician, Chem. Ber. 20, 1,369 (1887)).

The present invention provides compounds which are 1-N-substituted 1,4-dihydropyridazines of the following general formula I or their pharmaceutically acceptable bioprecursors:

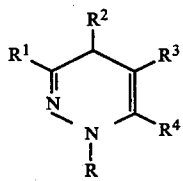

in which

R is straight-chain, branched or cyclic, saturated or unsaturated alkyl optionally interrupted in the alkyl chain by one or two oxygen atoms and/or substituted by halogen, carboalkoxy, dialkylamino or aryl or heteroaryl optionally having 1 or 2 identical or different substituents each of which is alkyl, aryl, aralkyl, halogen, cyano, nitro, trifluoromethyl, trifluoromethoxy, alkoxy or dialkylamino, or is a group $COR^5$, wherein:

$R^5$ is a straight-chain, branched or cyclic, saturated or unsaturated hydrocarbon radical which is optionally interrupted in the chain by one or two oxygen atoms and/or substituted by halogen or aryl, or is aryl or aralkyl, optionally substituted by 1 or 2 identical or different substituents each of which is alkyl, aryl, aralkyl, halogen, cyano, nitro, alkoxy, trifluoromethyl, trifluoromethoxy or dialkylamino, or is thienyl, furyl, pyridyl or quinolyl, or $R^5$ is a group $OR^6$, wherein:

$R^6$ is a straight-chain, branched or cyclic, saturated or unsaturated hydrocarbon radical which is optionally interrupted in the chain by one or two oxygen atoms, or is thienyl, furyl or pyridyl or aryl or aralkyl, optionally substituted by 1 or 2 identical or different substituents each of which is alkyl, aryl, aralkyl, halogen, cyano, nitro, alkoxy, trifluoromethyl, trifluoromethoxy or dialkylamino.

$R^1$ is a straight-chain, branched or cyclic, saturated or unsaturated hydrocarbon radical which is optionally interrupted in the chain by one or two oxygen and/or sulphur atoms and/or substituted by halogen or by phenoxy or phenyl, which is optionally substituted by halogen, cyano, dialkylamino, alkoxy, alkyl, trifluoromethyl, trifluoromethoxy or nitro, or by $\alpha$-, $\beta$- or $\gamma$-pyridyl or by amino having two identical or different substituents each of which is alkyl, alkoxyalkyl, aryl or aralkyl, said substituents optionally forming, together with the nitrogen atom of said amino, and optionally with a further hetero-atom, a from 5- to 7-membered heterocyclic ring, or is aryl or hetero-aryl which is thienyl, furyl, oxazolyl, isoxazolyl, thiazolyl, pyridyl, pyridazinyl, pyrimidyl, pyrazinyl, quinolyl, isoquinolyl, quinazolyl, or quinoxalyl, said aryl and hetero-aryl optionally having from 1 to 3 identical or different substituents each of which is phenyl, alkyl, alkenyl, alkinyl, alkoxy, alkenoxy, alkinoxy, alkylene, dioxyalkylene, halogen, trifluoromethyl, trifluoromethoxy, alkylamino, nitro, cyano, azido, carbalkoxy, $SO_m$-alkyl or $SO_m$-trifluoroalkyl wherein m is 0, 1 or 2, $R^2$ is aryl or hetero-aryl which is thienyl, furyl, oxazolyl, isoxazolyl, thiazolyl, pyridyl, pyridazinyl, pyrimidyl, pyrazinyl, quinolyl, isoquinolyl, quinazolyl or quinaxalyl, said aryl and hetero-aryl each optionally having from 1 to 3 identical or different substituents each of which is phenyl, alkyl, alkenyl, alkinyl, alkoxy, alkenoxy, alkinoxy, alkylene, dioxyalkylene, halogen, trifluoromethyl, trifluoromethoxy, alkylamino, nitro, cyano, azido, carbalkoxy, $SO_m$-alkyl or $SO_m$-trifluoroalkyl wherein m is 0, 1 or 2, $R^3$ is hydrogen or a group $COR^7$, wherein $R^7$ is alkyl, aryl or aralkyl, $R^4$ and $R^7$, optionally together with an oxygen, sulphur or nitrogen atom as a hetero-atom, optionally forming a from 5- to 7-membered ring or wherein $R^7$ is a group $OR^8$, wherein $R^8$ is a straight-chain, branched or cyclic, saturated or unsaturated hydrocarbon radical which is optionally interrupted in the chain by 1 or 2 oxygen or sulphur atoms or substituted by halogen or by phenoxy or phenyl, which is optionally substituted by halogen, cyano, dialkylamino, alkoxy, alkyl, trifluoromethyl or nitro, or by $\alpha$-, $\beta$- or $\gamma$-pyridyl or by amino which has two identical or different substituents each of which is alkyl, alkoxyalkyl, aryl or aralkyl, said substituents optionally forming, together with the nitrogen atom of the amino and optionally an oxygen or sulphur atom as a further hetero-atom, a from 5- to 7-membered heterocyclic ring, or $R^8$ is aryl which is optionally substituted by two identical or different substituents each of which is alkyl, aryl, aralkyl, alkoxy, halogen, cyano, nitro, trifluoromethyl, trifluoromethoxy or dialkylamino having 1 or 2 carbon atoms per alkyl moiety in each case, and $R^4$ is straight-chain or branched alkyl substituted by acyloxy or dialkylamino, or is perfluoroalkyl, or is aryl, aralkyl, thienyl, furyl or pyridyl, optionally having from 1 to 3 identical or different substituents each of which is phenyl, alkyl, alkenyl, alkinyl, alkoxy, alkenoxy, alkinoxy, alkylene, dioxyalkylene, halogen, trifluoromethyl, trifluoromethoxy, alkylamino, nitro, cyano, azido, carbalkoxy, $SO_m$-alkyl or $SO_m$-trifluoroalkyl wherein m is 0, 1 or 2.

The present invention also provides a process for the production of a compound according to the invention in which a 1,4-dihydropyridazine of the general formula II:

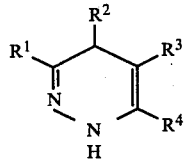

(II)

in which $R^1$, $R^2$, $R^3$ and $R^4$ have the same meaning as defined hereinbefore in formula I is first converted into the corresponding anion by reaction with a base of the general formula III:

B                       (III)

wherein B is a strong base, such as an alkali metal hydroxide, alkali metal alcoholate, alkali metal hydride or alkaline earth metal hydride, alkali metal amide, alkali metal dialkylamide or alkali metal alkyl, and the anion obtained is then reacted with an electrophilic compound of the general formula IV:

R—X                 (IV)

wherein:

R has the same meaning as defined hereinbefore in formula I, and

X represents a leaving group, such as halogen or a dialkyloxonium, dialkylsulphonium or trialkylammonium radical or is an arylsulphonic acid radical or a trifluoromethylsulphonic acid radical, generally in a suitable inert organic solvent, so as to produce the corresponding compound of formula I which is optionally converted into the corresponding free compound of formula I, respectively.

The free compounds of general formula I and their salts can be interconverted in any suitable manner; methods for such interconversion are known in the art.

The compounds of the invention have valuable pharmacological properties. Because of their circulation-influencing and spasmolytic actions, they can be used as antihypertensive agents, as vasodilators and as coronary therapeutic agents. The compounds according to the invention represent a novel class of substances for the treatment of the circulation and are thus to be regarded as an enrichment of pharmacy.

If 3-ethyl-1,4-dihydro-6-methyl-4-(3′nitrophenyl)-pyridazine-5-carboxylic acid ethyl ester, sodium hydride and chloromethyl ethyl ether are used as the starting materials, the course of the reaction can be represented by way of example by the following equation:

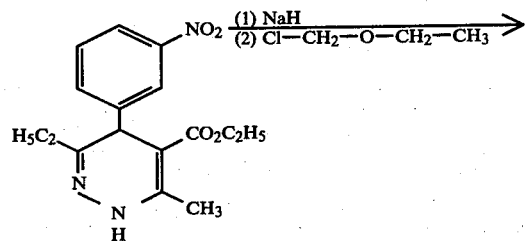

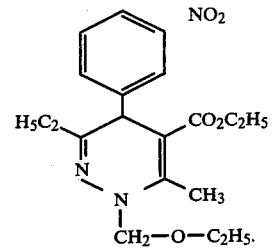

According to the procedure indicated, a 1,4-dihydropyridazine of the formula II is first converted into the corresponding anion with a suitable base of the formula III and the anion is subsequently reacted with an electrophile of the formula IV to give a 1-N-substituted 1,4-dihydropyridazine of the formula I.

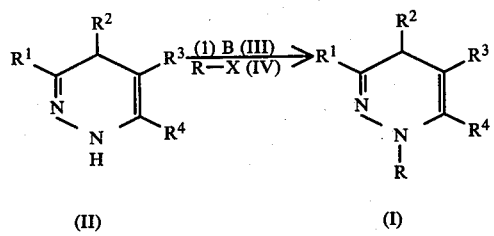

The substituents identified as R, $R^1$, $R^2$, $R^3$ and $R^4$ are defined as identified above. Preferably, $R^1$ is hydrogen, or preferably a straight-chain, branched or cyclic, saturated or unsaturated aliphatic hydrocarbon radical having up ti 8, especially up to 6, carbon atoms which is optionally interrupted in the chain by 1 to 2 oxygen and/or sulphur atoms and/or substituted by halogen, especially fluorine, or by phenoxy or phenyl, which is optionally substituted by halogen, especially fluorine or chlorine, cyano, dialkylamino having 1 or 2 carbon atoms per alkyl moiety in each case, alkoxy having from 1 to 4 carbon atoms, alkyl having from 1 to 4 carbon atoms, trifluoromethyl, trifluoromethoxy or nitro, or by α-, β- or γ-pyridyl or by amino having identical or two different substituents each of which is alkyl having up to 4 carbon atoms, alkoxyalkyl having up to 6, in particular up to 4, carbon atoms, phenyl or aralkyl, especially benzyl, said substituents optionally forming, together with the nitrogen atom of the amino and optionally an oxygen or sulphur atom as a further hetero-atom, a from 5- to 7-membered heterocyclic ring, or is phenyl or naphthyl or is thienyl, furyl, oxazolyl, isoxazolyl, thiazolyl, pyridyl, pyridazinyl, pyrimidyl, pyrazinyl, quinolyl, isoquinolyl, quinazolyl or quinoxalyl. The heterocyclic radicals mentioned, and in particular the phenyl radical, can contain 1 or 2 identical or different substituents, preferred substituents which may be mentioned being phenyl, straight-chain or branched alkyl having from 1 to 8, especially from 1 to 4, carbon atoms, cycloalkyl having from 3 to 7 carbon atoms, alkenyl or alkinyl having from 2 to 6 carbon atoms, especially 2 or 3 carbon atoms, alkoxy having preferably from 1 to 4, especially 1 or 2, carbon atoms, alkenoxy and alkinoxy having from 2 to 6, especially from 3 to 5, carbon atoms, dioxymethylene, halogen, especially fluorine or chlorine, most preferably fluorine, trifluoromethyl, trifluoromethoxy, nitro, cyano, azido, dialkylamino having preferably from 1 to 4, especially 1 or 2, carbon atoms per alkyl moiety, carbalkoxy having preferably from 2 to 4, in particular 2 or 3, carbon atoms, carboxamido, sulphonamido or $SO_m$-alkyl or trifluoromethyl, wherein m is 0, 1 or 2, or alkyl preferably having from 1 to 4, especially 1 or 2, carbon atoms.

$R^2$ preferably is phenyl or naphthyl or thienyl, furyl, oxazolyl, isoxazolyl, thiazolyl, pyridyl, pyridazinyl, pyrimidyl, pyrazinyl, quinolyl, isoquinolyl, quinazolyl or quinoxalyl. The heterocyclic radicals mentioned, and especially the phenyl radical, can contain 1 or 2 identical or different substituents, preferred substituents which may be mentioned being phenyl, straight-chain or branched alkyl having from 1 to 8, especially from 1 to 4, carbon atoms, cycloalkyl having from 3 to 7 carbon atoms, alkenyl or alkinyl having from 2 to 6 carbon atoms, especially 2 or 3 carbon atoms, alkoxy having preferably from 1 to 4, especially 1 or 2, carbon atoms, alkenoxy or alkinoxy having from 2 to 6, especially from 3 to 5, carbon atoms, dioxymethylene, halogen, especially fluorine or chlorine, most preferably fluorine, trifluoromethyl, tri-fluoromethoxy, nitro, cyano, azido, dialkylamino having preferably from 1 to 4, especially 1 or 2, carbon atoms per alkyl moiety, carbalkoxy having preferably from 2 to 4, especially 2 or 3, carbon atoms, carboxamido, sulphonamido or $SO_m$-alkyl wherein m is 0, 1 or 2 or alkyl preferably having from 1 to 4, especially 1 or 2, carbon atoms.

$R^3$ preferably is hydrogen or a group $COR^7$, wherein $R^7$ preferably is straight-chain or branched alkyl having from 1 to 4 carbon atoms, $R^4$ and $R^7$ optionally forming together with an oxygen, sulphur or nitrogen atom as a hetero-atom a from 5- to 7-membered, preferably a 5-membered or 6-membered, ring, or is phenyl, benzyl or dialkylamino having up to 4 carbon atoms per alkyl moiety, the alkyl groups optionally forming together with the nitrogen atom to which they are bonded and optionally an oxygen or sulphur atom as a further hetero-atom, a from 5- to 7-membered heterocyclic ring or is a group $OR^8$; wherein $R^8$ preferably is a straight-chain, branched or cyclic, saturated or unsaturated hydrocarbon radical having up to 8, especially up to 6, carbon atoms which is optionally interrupted in the chain by one or two oxygen or sulphur atoms and/or substituted by halogen, preferably by one or more fluorine atoms, or by phenoxy or phenyl, which is optionally substituted by halogen, especially fluorine or chlorine, cyano, dialkylamino having 1 or 2 carbon atoms per alkyl moiety in each case, alkoxy having from 1 to 4 carbon atoms, alkyl having from 1 to 4 carbon atoms, trifluoromethyl or nitro, or by α-, β- or γ-pyridyl or by amino, optionally having two identical or different substituents each of which is alkyl having up to 4 carbon atoms, alkoxyalkyl having up to 4 carbon atoms, phenyl or aralkyl, especially benzyl, said substituents optionally forming, together with the nitrogen atom of the amino and optionally an oxygen, sulphur or nitrogen atom as a further hetero-atom, the additional nitrogen atom substituted by a lower alkyl group, a from 5- to 7-membered heterocyclic ring, or is aryl especially phenyl optionally having 1 to 2 identical or different substituents, substituents which may be mentioned being straight-chain or branched alkyl having from 1 to 4 carbon atoms, alkoxy having 1 or 2 carbon atoms, halogen, especially fluorine or chlorine, cyano, methyl, trifluoromethoxy, dialkyl-amino having 1 or 2 carbon atoms per alkyl moiety in each case or nitro.

$R^4$ preferably is straight-chain or branched alkyl having from 1 to 4, especially 1 or 2, carbon atoms, perfluoroalkyl having preferably 1 to 2 carbon atoms, phenyl optionally substituted by nitro or methoxy or aralkyl, especially benzyl, or is heteraryl, especially thienyl, furyl or pyridyl.

The 1,4-dihydropyridazines used as starting materials are known from the literature or can be prepared by methods which are known from the literature (compare C. Paal and C. Koch, Chem. Ber. 36, 499 et seq. and 2,538 et seq. (1903); and W. J. Hale, J. Amer. Chem. Soc. 38, 2,833 (1916)).

Examples which may be mentioned are: e-ethyl-1,4-dihydro-6-methyl-4-phenyl-pyridazine-5-carboxylic acid ethyl ester, 3-ethyl-1,4-dihydro-6-methyl-4-(3'-nitrophenyl)-pyridazine-5-carboxylic acid ethyl ester, 3-ethyl-4-(3'-chlorophenyl)-1,4-dihydro-6-methyl-pyridazine-5-carboxylic acid ethyl ester, 3-ethyl-4-(2'chlorophenyl)-1,4-dihydro-6-methylpyridazine-5-carboxylic acid ethyl ester, 3-ethyl-1,4-dihydro-4-(3'methoxyphenyl)-6-methyl-pyridazine-5-carboxylic acid ethyl ester, 3-ethyl-1,4-dihydro-6-methyl-4-(2'trifluoromethylphenyl)-pyridazine-5-carboxylic acid ethyl ester, 3-ethyl-1,4-dihydro-6-methyl-4-(4'nitrophenyl)-pyridazine-5-carboxylic acid ethyl ester, 3-ethyl-4-(4'-chlorophenyl)-1,4-dihydro-6-methyl-pyridazine-5-carboxylic acid ethyl ester, 3-ethyl-1,4-dihydro-6-methyl-4-(3'-nitrophenyl)-pyridazine-5-carboxylio acid n-hexyl ester, 3-ethyl-1,4-dihydro-6-methyl-4-(3'-nitrophenyl)-pyridazine-5-carboxylic acid β-methoxyethyl ester, 3-ethyl-, 1,4-dihydro-6-methyl-4-(3'nitrophenyl)-pyridazine-5-carboxylic acid benzyl ester, 3-ethyl-1,4-dihydro-6-methyl-4-(3'-nitrophenyl)-pyridazine-5-carboxylic acid t-butyl ester, 3-ethyl-1,4-dihydro-6-methyl-4-(3'-nitrophenyl)-pyridazine-5-carboxylic acid β-n-butoxyethyl ester, 3-ethyl-4-(3'-cyanophenyl)-1,4-dihydro-6-methyl-pyridazine-5-carboxylic acid ethyl ester, 3-ethyl-1,4-dihydro-6-methyl-4-(3'-nitrophenyl)-pyridazine-5-carboxylic acid cyclopentyl ester, 3-ethyl-1,4-dihydro-6-methyl-4-(3'nitrophenyl)-pyridazine-5-carboxylic acid furfuryl ester, 3-ethyl-1,4-dihydro-6-methyl-4-(3'-nitrophenyl)-pyridazine-5-carboxylic acid propargyl ester, 3-ethyl-1,4-dihydro-6-methyl-4-α-naphthyl-pyridazine-5-carboxylic acid ethyl ester, 3-ethyl-1,4-dihydro-4-(fur-2-yl)-6-methyl-pyridazine-5-carboxylic acid ethyl ester, 3-ethyl-1,4-dihydro-4-(thien-2-yl)-pyridazine-5-carboxylic acid ethyl ester, 1,4-dihydro-6-methyl-4-phenyl-3-(thien-2-yl)-pyridazine, 4-(3'-chlorophenyl)-1,4-dihydro-6-methyl-3-(thien-2-yl)-pyridazine, 1,4-dihydro-3,4,6-tri-(thien-2-yl)-pyridazine, 1,4-dihydro-6-methyl-4-phenyl-3-(thien-2-yl)-pyridazine-5-carboxylic acid methyl ester, 1,4-dihydro-3,4-diphenyl-6-methyl-pyridazine-5-carboxylic acid methyl ester, 4-(3'-chlorophenyl)-1,4-dihydro-6-methyl-3-(thien-2-yl)-pyridazine-5-carboxylic acid methyl ester, 4-(3'-chlorophenyl)-1,4-dihydro-6-methyl-3-phenyl-pyridazine-5-carboxylic acid methyl ester, 1,4-dihydro-3-(fur-2-yl)-6-methyl-4-phenyl-pyridazine-5-carboxylic acid ethyl ester, 3-(3'-chlorophenyl)-1,4-dihydro-6-methyl-4-phenyl-pyridazine-5-carboxylic acid methyl ester, 4-(2'-chlorophenyl)-1,4-dihydro-3-(fur-2-yl)-6-methyl pyridazine-5-carboxylic acid methyl ester, 3,4-di-(3'-chlorophenyl)-1,4-dihydro-6-methyl-pyridazine-5-carboxylic acid methyl ester, 3-cyclohexyl-1,4-dihydro-6-methyl-4-(4'-trifluoromethylphenyl)-pyridazine-5-carboxylic acid t-butyl ester, 3,6-diethyl-1,4- dihydro-4-(2'-trifluoromethylphenyl)-pyridazine-5-carboxylic acid ethyl ester, 3-ethyl-1,4,5,6,7,8-hexahydro-5-oxo-4-(3'-nitro-phenylcinnoline and 3-(β-ethoxyethyl)-1,4-dihydro-6-methyl-4-(2'-trifluoromethylphenyl)-pyridazine-5-carboxylic acid n-propyl ester.

The bases of the formula III used as starting materials are known from the literature and are commercially available (compare L. Fieser and M Fieser, Reagents for Organic Synthesis, volume 5, John Wiley and Sons, New York, N.Y., 1975).

Examples which may be mentioned are: sodium hydroxide, potassium hydroxide, sodium methylate, potassium t-butylate, sodium hydride, sodium amide, potassium hydride, lithium bis-(trimethylsilyl)amide, lithium diisopropylamide, lithium iso-propylcyclohexylamide, methyl-lithium and n-butyl-lithium.

In formula IV,

R preferably is a straight-chain, branched or cyclic, saturated or unsaturated aliphatic hydrocarbon radical, having up to 8, especially 6, carbon atoms (particularly alkyl radicals) which is optionally interrupted in the chain by 1 or 2 oxygen atoms and/or substituted by halogen, especially one or more fluorine atoms, by dialkylamino having 1 or 2 carbon atoms per alkyl moiety in each case, by carboalkoxy having a saturated or unsaturated alkoxy, preferably with up to 8 carbon atoms, especially up to 6 carbon atoms, or by aryl or hetaryl, especially phenyl, which optionally has 1 or 2 identical or different substituents, substituents which jay be mentioned being straight-chain or branched alkyl having from 1 to 4 carbon atoms, methoxy, halogen, especially fluorine or chlorine, cyano, nitro, trifluoromethyl, trifluoromethoxy or dialkylamino having 1 or 2 carbon atoms per alkyl moiety in each case, or is a group $COR^5$,
wherein:

$R^5$ is a straight-chain, branched or cyclic, saturated or unsaturated aliphatic hydrocarbon radical having preferably up to 8, especially 6, carbon atoms which is optionally interrupted in the chain by 1 oxygen atom and/or substituted by halogen, preferably one or more fluorine atoms, or by aryl especially phenyl,
or wherein:

$R^5$ is aryl or aralkyl, especially phenyl or benzyl which optionally has 1 or 2 identical or different substituents each of which is straight-chain or branched alkyl having preferably from 1 to 4 carbon atoms, methoxy, halogen, especially fluorine or chlorine, cyano, nitro, trifluoromethyl, trifluoromethoxy or dialkylamino having 1 or 2 carbon atoms per alkyl moiety, or is thienyl, furyl, pyridyl or quinolyl,
or wherein:

$R^5$ is a group $OR^6$;
wherein:

$R^6$ is a straight-chain, branched or cyclic, saturated or unsaturated hydrocarbon radical having preferably up to 8, especially 6, carbon atoms which is optionally interrupted in the chain by an oxygen atom and/or substituted by halogen, preferably one or more fluorine atoms or by dialkylamino having 1 or 2 carbon atoms per alkyl moiety in each case, or $R^6$ is aryl or aralkyl, especially phenyl or benzyl, optionally having 1 or 2 identical or different substituents each of which is straight-chain or branched alkyl having from 1 to 4 carbon atoms, methoxy, halogen, in particular fluorine and chlorine, cyano, nitro, trifluoromethyl-, trifluoromethoxy or dialkylamino having 1 or 2 carbon atoms per alkyl moiety in each case, and X is a leaving radical, such as halogen, especially chlorine, bromine or iodine, or a dialkyloxonium, dialkylsulphonium or trialkylammonium radical having preferably from 1 to 4 carbon atoms per alkyl moiety or is the p-toluenesulphonic acid radical or trifluoromethylsulphonic acid radical.

The electrophiles used as starting materials are known from the literature in some cases, or they can be prepared by methods which are known from the literature (compare L. Fieser and M. Fieser, Reagents for Organic Synthesis, volume I and II, John Wiley & Sons, New York, N.Y., 1967).

Examples which may be mentioned are: ethyl bromide, ethyl iodide, n-propyl iodide, i-propyl iodide, n.butyl bromide, sec.-butyl bromide, i-butyl iodide, chloromethyl ethyl ether, perfluoroethyl iodide, cyclopentyl bromide, triethyloxonium tetrafluoborate, propargyl bromide, allyl bromide, benzyl bromide, benzyl chloride, p-benzyloxybenzyl chloride, m- and p-chlorobenzyl bromide, 3,4-dichlorobenzyl bromide, o-, m- and p-nitrobenzyl bromide, 2-methoxy-4-nitrobenzyl bromide, 4-tri-fluoromethylbenzyl chloride, bromoacetic acid methyl ester, chloroacetic acid ethyl ester, 2-bromopropionic acid ethyl ester, 3-bromo-propionic acid methyl ester, bromoacetic acid hexyl ester, acetyl chloride, acetyl bromide, propionyl chloride, n-butyryl chloride, cyclohexanecarboxylic acid chloride, crotonyl chloride, methoxyacetyl chloride, hexanoyl chloride, phenyl-acetyl chloride, m-nitrophenylacetyl bromide, benzoyl chloride, m-nitrobenzoyl chloride, 3,4-dichlorobenzoyl chloride, 4-cyanobenzoyl chloride, m-trifluoromethylbenzoyl chloride, m-tri-fluoromethoxybenzoyl chloride, p-dimethylaminobenzoyl chloride, p-fluorobenzyl chloride, m-, p- and o-toluyl chloride, 2-furoyl chloride, thiophene-2-carboxylic acid chloride, isonicotinic acid chloride, nicotinic acid chloride, picolinic acid chloride, cinnamic acid chloride, m-chlorocinnamic acid chloride, chloroformic acid methyl ester, chloroformic acid ethyl ester, chloroformic acid n-butyl ester, chloroformic acid i-butyl ester, chloroformic acid benzyl ester, chloroformic acid phenyl ester, chloroformic acid 4-nitrophenyl ester, chloroformic acid perfluoroethyl ester and chloroformic acid p-methoxyphenyl ester.

Possible diluents are all the inert organic solvents. These include, preferably, ethers, such as dioxane, diethyl ether, tetrahydrofurane and glycol dimethyl ether, or dimethylformamide, dimethylsulphoxide, acetonitrile, pyridine and hexamethylphosphoric acid triamide.

The reaction temperatures can be varied within a relatively wide range. In general, the reaction is carried out at from $-78°$ C. to $100°$ C., preferably in the range from $-20°$ C. to $+20°$ C.

The reaction can be carried out in an inert atmosphere under ambient pressure, but also under superatmospheric pressure. In general, the reaction is carried out under ambient pressure under an inert gas, such as very pure nitrogen or argon.

In carrying out the process according to the invention, 1 mol of the 1,4-dihydropyridazine of the formula II is generally reacted with approximately 1 mol of the base of the formula III in a suitable solvent. When the reaction has ended, the electrophile of the formula IV is added, in dilute form, for the second reaction stage and the reaction is brought to completion using a suitable working-up procedure.

The isolation and purification of the compounds according to the invention are preferably carried out by distilling off any solvent in vacuo, if appropriate after separating off insoluble materials, and recrystallising the residue, which in some cases is obtained in the crystalline form only after cooling with ice, from a suitable solvent.

The above production process is only given for illustration. Thus the preparation of the compounds of the formula I is not limited to this process and any modification of this process can be applied in the same manner to the preparation of the compounds according to the invention.

Depending on the choice of the starting substances, the compounds according to the invention can exist in stereoisomeric forms which either behave as mirror images (enantiomers) or do not behave as mirror images (diastereomers). The present invention relates to both the antipodes and the racemic forms as well as the diastereomer mixtures. The racemic forms can be separated into the stereoisomerically single constituents in a known manner, as can the diastereomers (compare, for example, E. L. Eliel, Stereochemistry of Carbon Compounds, McGraw Hill, 1962).

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optionally active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-touyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

In addition to the compounds of the working examples listed below, the following active compounds according to the invention can be obtained by methods analogous to those of the working examples:

1,3-diethyl-1,4-dihydro-6-methyl-4-(3'-nitrophenyl)-pyridazine-5-carboxylic acid ethyl ester, 3-ethyl-4-(3'-chlorophenyl)-1,4-dihydro-1,6-dimethyl-pyridazine-5-carboxylic acid ethyl ester, 3-ethyl-4-(2'-chlorophenyl)-1,4-dihydro-1-isopropyl-6-methyl-pyridazine-5-carboxylic acid methyl ester, 3-ethyl-1-cyclopentyl-1,4-dihydro-4-(3'-methoxyphenyl)-6-methylpyridazine-5-carboxylic acid ethyl ester, 1-ethoxymethyl-3-ethyl-1,4-dihydro-6-methyl-4-(2'-trifluoromethylphenyl)-pyridazine-5-carboxylic acid i-propyl ester, 3-ethyl-1,4-dihydro-6-methyl-4-(3'-nitrophenyl)-1-(3',3',3'-trifluoropropyl)-pyridazine-5-carboxylic acid ethyl ester, 3-ethyl-1-carboethoxymethyl-1,4-dihydro-6-methyl-4-(3'-nitrophenyl)-pyridazine-5-carboxylic acid β-methoxyethyl ester, 3-ethyl-1,4-dihydro-6-methyl-4-(3'-nitrophenyl)-1-phenyl-acetylpyridazine-5-carboxylic acid ethyl ester, 3-ethyl-1,4-dihydro-6-methyl-4-(3'-nitrophenyl)-1-(4'-trifluoromethylphenylacetyl)pyridazine-5-carboxylic acid ethyl ester, 3-ethyl-1,4-dihydro-6-methyl-4-(3'-nitrophenyl)-1-(3'-nitrobenzoyl)-pyridazine-5-carboxylic acid t-butyl ester, 3-ethyl-1,4-dihydro-1,6-dimethyl-4-(3'-nitrophenyl)-pyridazine-5-carboxylic acid β-n-butoxyethyl ester, 3-ethyl-4-(3'-cyanophenyl)-1,4-dihydro-1-n-propyl-6-methyl-pyridazine-5-carboxylic acid ethyl ester, 3-ethyl-1-carboethoxymethyl-1,4-dihydro-6-methyl-4-(2'-nitrophenyl)pyridazine-5-carboxylic acid n-propyl ester, 3-ethyl-1-carboethoxy-1,4-dihydro-6-methyl-4-(2'-nitrophenyl)-pyridazine-5-carboxylic acid ethyl ester, 3-ethyl-1,4-dihydro-6-methyl-4-(3'-nitrophenyl)-1-(thien-2-yl-carbonyl)-pyridazine-5-carboxylic acid ethyl ester, 3-ethyl-1,4-dihydro-6-methyl-4-(2'-nitrophenyl)-1-(pyrid-2-yl-carbonyl)-pyridazine-5-carboxylic acid β-methoxyethyl ester, 1,4-dihydro-3,6-dimethyl-1-(fur-2-yl-carbonyl)-4-(4'-trifluoromethoxyphenyl)-pyridazine-5-carboxylic acid i-propyl ester, 3-ethyl-1-cinnamoyl-1,4-dihydro-6-methyl-4-(2'-trifluoromethylphenyl)-pyridazine-5-carboxylic acid benzyl ester, 1-carboethoxypropyl-1,4-dihydro-6-methyl-4-(3'-nitrophenyl)-3-(thien-2-yl)-pyridazine-5-carboxylic acid methyl ester, 1-carbobenzyloxy-1,4-dihydro-3,4-dimethyl-6-methyl-pyridazine-5-carboxylic acid ethyl ester, 1-carbophenoxy-3-cyclohexyl-1,4-dihydro-6-methyl-4-(4'-trifluoromethylphenyl)-pyridazine-5-carboxylic acid i-propyl ester, 3,4-di-(3'-chlorophenyl)-1,4-dihydro-1,6-dimethyl-pyridazine-5-carboxylic acid methyl ester, 1-carboethoxymethyl-1,4-dihydro-3-(fur-2-yl)-6-methyl-4-(2'-nitrophenyl)-pyridazine-5-carboxylic acid ethyl ester, 1-carboethoxy-3,6-diethyl-1,4-dihydro-4-(2'-trifluoromethylphenyl)-pyridazine-3-carboxylic acid ethyl ester, 3-(β-ethoxyethyl)-1-carbobenzyloxy-1,4-dihydro-6-methyl-4-(2'-trifluoromethylphenyl)-pyridazine-5-carboxylic acid n-propyl ester, 1,4-dihydro-n-methyl-3,4,6-tri-(thien-2-yl)-pyridazine and 1,4-dihydro-1-(thien-2-yl-carbonyl)-3,4,6-tri-(thien2-yl)-pyridazine.

Compounds of the formula I in which:

R is straight-chain, branched or cyclic alkyl or alkenyl having up to 8 carbon atoms, the alkyl chain being optionally interrupted by an oxygen atom or substituted by halogen, especially fluorine, dialkylamino having 1 or 2 carbon atoms per alkyl moiety, carboalkoxy having up to 6 carbon atoms or phenyl optionally substituted by one or two identical or different substituents each of which is chlorine, nitro, cyano, trifluoromethyl, trifluoromethoxy, methoxy or dialkylamino having 1 or 2 carbon atoms per alkyl moiety, or is a grou $COR^5$; wherein:

$R^5$ is either straight-chain, branched or cyclic alkyl or alkenyl having up to 8 carbon atoms, the carbon chain being optionally interrupted by an oxygen atom or substituted by halogen, especially fluorine, aryl, especially phenyl, or is aryl or aralkyl, optionally having 1 or 2 identical or different substituents each of which is alkyl or alkoxy having 1 or 2 carbon atoms or halogen, nitro, cyano, trifluoromethoxy, trifluoromethyl or dialkylamino having 1 or 2 carbon atoms per alkyl moiety, or is thienyl, furyl or pyridyl, or $R^5$ is a group $OR^6$, wherein:

$R^6$ is straight-chain, branched or cyclic alkyl or alkenyl having up to 8 carbon atoms and optionally interrupted by an oxygen atom or substituted by halogen, especially fluorine, or dialkylamino having 1 or 2 carbon atoms per alkyl moiety, or $R^6$ is aryl or aralkyl optionally having 1 or 2 identical or different substituents each of which is alkyl having 1 or 2 carbon atoms, methoxy, halogen, nitro, cyano, trifluoromethoxy, trifluoromethyl or dialkylamino having 1 or 2 carbon atoms per alkyl moiety, $R^1$ is hydrogen, straight-chain, branched or cyclic alkyl or alkenyl having up to 8 carbon atoms, the alkyl chain being optionally interrupted by an oxygen atom or substituted by halogen, especially fluorine, phenoxy, halogenophenyl, nitrophenyl, pyridyl, furyl, thienyl or diethylamine or benzylalkylamine having 1 or 2 carbon atoms in the alkyl moiety in each case, or os pyridyl, furyl or thienyl or is phenyl optionally substituted by one or two identical or different substituents each of which is halogen, nitro, cyano, trifluoromethyl, trifluoromethoxy or alkyl or alkoxy having in each case from 1 to 4, especially 1 or 2, carbon atoms, $R^2$ is phenyl optionally substituted by one or two identical or different substituents each of which is halogen, nitro, cyano, trifluoromethyl, trifluoromethoxy or alkyl or alkoxy having in each case from 1 to 4 especially 1 or 2, carbon atoms, or is pyridyl, thienyl or furyl, $R^3$ is hydrogen or a group $COR^7$,
wherein:

$R^7$ is alkyl having from 1 to 4 carbon atoms, or $R^4$ and $R^7$ can together optionally with a hetero-atom such as oxygen, form a 5-membered or 6-membered ring, or is a group $OR^8$,
wherein:

$R^8$ is straight-chain, branched or cyclic alkyl or alkenyl having up to 6 carbon atoms, the alkyl chain being optionally interrupted by an oxygen atom or substituted by phenoxy, halogenophenyl, nitrophenyl, pyridyl, dialkylamino having in each case 1 or 2 carbon atoms in the alkyl moiety or benzyl-alkylamino having 1 or 2 carbon atoms in the alkyl moiety in each case, and $R^4$ is alkyl having 1 or 2 carbon atoms which can form optionally together with an oxygen as a hetero-atom and together with $R^8$, a 5-membered or 6-membered ring or is phenyl, benzyl, pyridyl or thienyl, are particularly suitable as circulation-influencing and spasmolytically active medicaments.

1-N-substituted 1,4-dihydropyridazines of the general formula I in which:

R is straight-chain or branched alkyl having from 1 to 4 carbon atoms, the alkyl chain being optionally interrupted by an oxygen or substituted by fluorine or carboalkoxy having up to 4 carbon atoms or by phenyl optionally having one or two identical or different substituents each of which is fluorine, chlorine, nitro, cyano, trifluoromethyl, trifluoromethoxy, methoxy or dimethylamino, or is a group $COR^5$,
wherein:

$R^5$ is straight-chain or branched alkyl having from 1 to 4 carbon atoms which is optionally interrupted by an oxygen atom or substituted by fluorine or phenyl,
or wherein:

$R^5$ is phenyl or benzyl, which is optionally substituted by methyl, methoxy, halogen, nitro, cyano or trifluoromethyl,
or wherein:

$R^5$ is a group $OR^6$,
wherein:

$R^6$ is straight-chain or branched alkyl having from 1 to 4 carbon atoms and optionally interrupted by an oxygen atom or optionally substituted by fluorine or dimethylamino, or $R^6$ is phenyl or benzyl, which is optionally substituted by methyl, methoxy, halogen, nitro, cyano, trifluoromethoxy, trifluoromethyl or dimethylamino, $R^1$ is hydrogen or straight-chain or branched alkyl having from 1 to 4 carbon atoms, the alkyl chain being optionally interrupted by one oxygen atom or substituted by halogen, especially fluorine, $R^2$ is phenyl optionally substituted by halogen, especially fluorine or chlorine, nitro, cyano, trifluoromethyl, trifluoromethoxy or alkyl or alkoxy having 1 or 2 carbon atoms in each case, or is pyridyl, thienyl or furyl, $R^3$ represents the group $COR^7$ or the group $COOR^8$,
wherein:

$R^7$ and $R^8$ each represent straight-chain or branched alkyl having from 1 to 4 carbon atoms, the alkyl chain being optionally interrupted by an oxygen atom, or $R^7$, together with the substituent $R^4$, and optionally an oxygen atom, forms a 5-membered or 6-membered ring, and $R^4$ represents alkyl having 1 or 2 carbon atoms, are of particular interest.

For the purpose of this specification the term "pharmaceutically acceptable bioprecursor" of an active compound of the invention means a compound having a structural formula different from the active compound but which nonetheless, upon administration to a warm-blooded animal, is converted in the patient's body to the active compound.

The new compounds have a broad and diverse spectrum of pharmacological action.

In particular, the following main actions can be demonstrated in animal experiments:

(1) On parenteral, oral and perlingual administration the compounds produce a distinct and long-lasting dilation of the coronary vessels. This action on the coronary vessels is intensified by a simultaneous nitrite-like effect of reducing the load on the heart. They influence or modify the heart metabolism in the sense of an energy saving.

(2) The excitability of the stimulus formation and excitation conduction system within the heart is lowered, so that an antifibrillation action which can be demonstrated at therapeutic doses results.

(3) The tone of the smooth muscle of the vessels is greatly reduced under the action of the compounds. This vascularspasmolytic action can take place in the entire vascular system or can manifest itself more or less isolated in circumscribed vascular regions (such as, for example, the central nervous system).

(4) The compounds lower the blood pressure of warm-blooded animals and can thus be used as antihypertensive agents.

(5) The compounds have strongly muscular-spasmolytic actions which manifest themselves on the smooth muscle of the stomach, the intestinal tract, the urogenital tract and the respiratory system.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily doese will depend on whether the medicament is to be administered once or, for example, twice, three times or four times a day respectively.

The pharmaceutical compositions according to the invention may, for example, take the form of suspensions, solutions and emulsions of the active ingredients in aqueous or non-aqueous diluents or syrups.

The diluents to be used in pharmaceutical compositions (e.g. granulates) adapted to be formed into tablets, dragees, capsules and pills include the following: (a) fillers and extenders, e.g starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agaragar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelope and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid] or mixtures of these diluents.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil] glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxde, bentonite, agar-agar and tragacanth or mixture thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% most preferably from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 0.05 to 500 mg intravenously or from 0.5 to 1000 mg orally of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in warm-blooded animals, which comprises administering to the animals a compound of the invention alone or in admixture with a diluent or in the form of a medicament according to the invention.

It is envisaged that these active compounds will be administered perorally (especially perlingually) parenterally (for example intramuscularly, intraperiotoneally or intravenously) or rectally, preferably orally or parenterally. Preferred pharmaceutical compositions and medicaments are therefore those adapted for oral or intravenous administration, such as tablets, pills, capsules or dragees or injection solutions or suspensions or ampoules thereof, respectively. Administration in the method of the invention is preferably orally or intravenously.

In general it has proved advantageous to administer amounts of from 0.001 to 10 mg, preferably from 0.05 to 5 mg, intravenously, or from 0.01 to 20 mg, preferably from 0.1 to 5 mg, orally, per kg of body weight per day to achieve effective results. Nevertheless, it can at times be necessary to deviate from those dosages rates and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

PREPARATION EXAMPLES

Example 1

1,4-dihydro-4-phenyl-4,3,6-trimethyl-pyridazine-5-carboxylic acid ethyl ester

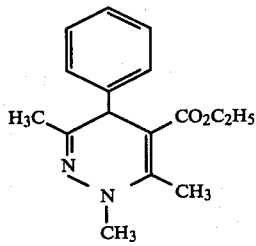

25.8 g (0.10 mol) of 1,4-dihydro-3,6-dimethyl-4-phenylpyridazine-5-carboxylic acid methyl ester in 100 ml of absolute tetrahydrofurane are added dropwise to 3.2 g (0.12 mol) of sodium hydride in 20 ml of absolute tetrahydrofurane under nitrogen and with the exclusion of moisture, and the mixture is stirred for about 30 minutes, until the evolution of hydrogen has ended. After cooling the mixture to −15° C., 15.7 g (0.11 mol) of methyl iodide in 10 ml of tetrahydrofurane are added dropwise and the mixture is stirred at −15° C. for 1 hour and, after warming to room temperature, for a further hour. The mixture is then poured into one liter of water, the oil which has precipitated is extracted with chloroform and the organic phase is washed with water, dried with sodium sulphate and concentrated. The residue is distilled in vacuo.

Boiling point: 181° C. (0.1 mm Hg).
Yield: 66% of theory.

EXAMPLE 2

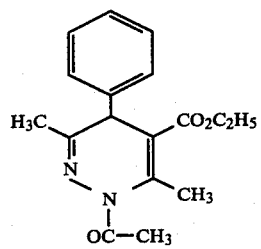

Analogously to Example 1, 1-acetyl-1,4-dihydro-3,6-dimethyl-4-phenyl-pyridazine-5-carboxylic acid ethyl ester of boiling point 196° C. (0.1 mm Hg) was obtained by reacting 1,4-dihydro-3,6-dimethyl-4-phenyl-pyridazine-5-carboxylic acid ethyl ester with lithium diisopropylamide and acetyl chloride in diethyl ether.

Yield: 57% of theory.

EXAMPLE 3

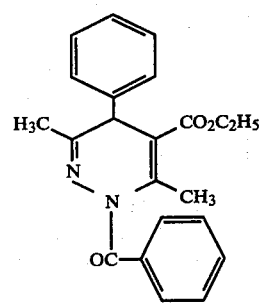

Analogously to Example 1, 1,benzoyl-1,4-dihydro-3,6-dimethyl-4-phenyl-pyridazine-5-carboxylic acid ethyl ester of melting point 115° C. (methanol) was obtained by reacting 1,4-dihydro-3,6-dimethyl-4-phenyl-pyridazine-5-carboxylic acid ethyl ester with lithium isopropylcyclohexylamide and benzoyl chloride in glycol dimethyl ether.

Yield: 50% of theory.

EXAMPLE 4

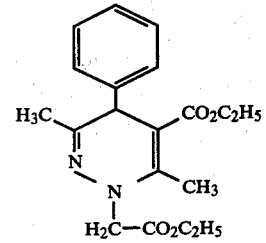

Analogously to Example 1, 1-carboethoxy-methyl-1,4-di-hydro-3,6-dimethyl-4-phenyl-pyridazine-5-carboxylic acid ethyl ester of boiling point 210° C. (0.2 mm Hg) is obtained by reacting 1,4-dihydro-3,6-dimethyl-4-phenyl-pyridazine-5-carboxylic acid ethyl ester with sodium hydride and bromoacetic acid ethyl ester in dioxane.

Yield: 64% of theory.

EXAMPLE 5

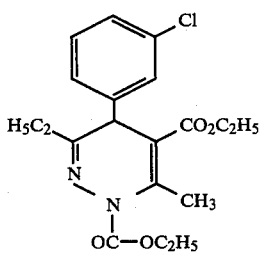

Analogously to Example 1, 3-ethyl-1-carboethoxy-4-(3'-chlorophenyl)-1,4-dihydro-6-methyl-pyridazine-5-carboxylic acid ethyl ester of boiling point 208° C. (0.2 mm Hg) is obtained by reacting 3-ethyl-4-(3'-chlorophenyl)-1,4-dihydro-6-methyl-pyridazine-5-carboxylic acid ethyl ester with sodium methylate and chloroformic acid ethyl ester in diethyl ether.

Yield: 89% of theory.

EXAMPLE 6

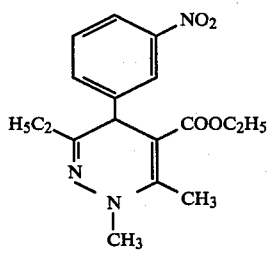

Analogously to Example 1, the compound 3-ethyl-1,4-dihydro-1,6-dimethyl-4-(3-nitrophenyl)-pyridazine-5-carboxylic acid ethyl ester of boiling point 242° C. (0.1 mm Hg) is obtained by reacting 3-ethyl-1,4-dihydro-6-methyl-4-(3-nitrophenyl)-pyridazine-5-carboxylic acid ethyl ester with sodium amide and methyl iodide in diethyl ether.

Yield: 68% of theory.

What is claimed is:

1. A compound which is 1-N-substituted 1,4-dihydropyridazine of the formula or its pharmaceutically acceptable bioprecursors:

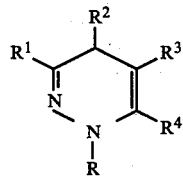

(I)

in which:

R is a straight-chain or branched alkyl having 1 to 4 carbon atoms optionally substituted by fluorine or carboalkoxy having up to 4 carbon atoms, or is a group $COR^5$ wherein $R^5$ is straight-chain or branched alkyl having from 1 to 4 carbon atoms optionally substituted by fluorine or phenyl or wherein $R^5$ is phenyl or benzyl which is optionally substituted by methoxy, halogen or nitro or wherein $R^5$ is a group $OR^6$ wherein $R^6$ is straight-chain or branched alkyl having from 1 to 4 carbon atoms or $R^6$ is phenyl or benzyl which is optionally substituted by methoxy, halogen or nitro $R^1$ is straight-chain or branched alkyl having from 1 to 4 carbon atoms optionally being substituted by halogen, $R^2$ is phenyl optionally substituted by halogen, nitro, cyano or trifluoromethyl, $R^3$ represents the group $COOR^8$ wherein $R^8$ represents straight-chain or branched alkyl having from 1 to 4 carbon atoms, the alkyl chain being optionally interrupted by an oxygen atom and $R^4$ represents alkyl having 1 or 2 carbon atoms.

2. A compound according to claim 1 which is 1-acetyl-1,4-dihydro-3,6-dimethyl-4-phenyl-pyridazine-5-carboxylic acid ethyl ester.

3. A compound according to claim 1 which is 1-carboethoxy-methyl-1,4-dihydro-3,6-dimethyl-4-phenyl-pyridazine-5-carboxylic acid ethyl ester.

4. A compound according to claim 1 which is 3-ethyl-1,4-dihydro-1,6-dimethyl-4-(3-nitrophenyl)-pyridazine-5-carboxylic acid ethyl ester.

5. A pharmaceutical composition containing as an active ingredient an effective amount of a compound according to claim 1 in admixture with a solid or liquefied gaseous diluent or in admixture with a liquid diluent other than a solvent of a molecular weight less than 200 except in the presence of a surface-active agent.

6. A pharmaceutical composition of claim 5 in the form of a sterile or physiologically isotonic aqueous solution.

7. A pharmaceutical composition according to claim 5 containing from 0.5 to 90% by weight of the said active ingredient.

8. A medicament in dosage unit form comprising an effective amount of a compound according to claim 1 together with an inert pharmaceutical carrier.

9. A medicament of claim 8 in the form of tablets, pills, dragees, capsules, ampoules, or suppositories.

10. A method of combating circulatory disorders in warm-blooded animals which comprises administering to the animals an effective amount of an active compound according to claim 1 either alone or in admixture with a diluent or in the form of a medicament.

11. A method according to claim 10 in which the active compound is administered orally in an amount of from 0.01 to 20 mg per kg body weight per day.

12. A method according to claim 10 in which the active compound is administered intravenously in an amount of from 0.001 to 10 mg per kg body weight per day.

13. A method according to claim 11 or 12 in which the animals are ruminants.

* * * * *